US012569471B2

(12) United States Patent
Breder

(10) Patent No.: US 12,569,471 B2
(45) Date of Patent: *Mar. 10, 2026

(54) METHOD OF TREATMENT OF CNS DISORDERS

(71) Applicant: Supernus Pharmaceuticals, Inc., Rockville, MD (US)

(72) Inventor: Christopher D. Breder, Bethesda, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,681

(22) Filed: Jul. 17, 2023

(65) Prior Publication Data

US 2023/0355589 A1 Nov. 9, 2023

Related U.S. Application Data

(63) Continuation of application No. 16/678,848, filed on Nov. 8, 2019, now Pat. No. 11,911,368, which is a continuation of application No. 14/795,983, filed on Jul. 10, 2015, now abandoned, which is a continuation of application No. 13/512,706, filed as application No. PCT/US2010/058745 on Dec. 2, 2010, now abandoned.

(60) Provisional application No. 61/282,011, filed on Dec. 2, 2009.

(51) Int. Cl.
*A61K 31/4188* (2006.01)
*A61K 9/00* (2006.01)
*A61K 31/00* (2006.01)

(52) U.S. Cl.
CPC ........ *A61K 31/4188* (2013.01); *A61K 9/0053* (2013.01); *A61K 31/00* (2013.01)

(58) Field of Classification Search
CPC .. A61K 31/00; A61K 31/4188; A61K 9/0053; A61P 25/00; A61P 25/22; A61P 25/24; A61P 25/28
See application file for complete search history.

(56) References Cited

U.S. PATENT DOCUMENTS

| | | | |
|---|---|---|---|
| 3,931,217 A | 1/1976 | Metlesics et al. | |
| 8,293,779 B2 | 10/2012 | Konoval | |
| 2002/0161002 A1* | 10/2002 | Epstein ................. | A61K 31/00 |
| | | | 514/649 |
| 2003/0180352 A1 | 9/2003 | Patel et al. | |
| 2009/0136593 A1 | 5/2009 | Konofal | |
| 2009/0318520 A1 | 12/2009 | Kovacs et al. | |
| 2011/0183009 A1 | 7/2011 | Konofal | |

FOREIGN PATENT DOCUMENTS

| | | |
|---|---|---|
| WO | WO 93/21917 A1 | 11/1993 |
| WO | WO-02/053104 A2 | 7/2002 |
| WO | WO 2007/116076 A1 | 10/2007 |

OTHER PUBLICATIONS

Bittencourt et al,. "Mazindol and lidocaine are antinociceptives in the mouse formalin model: involvement of dopamine receptor," European Journal of Pharmacology, 1997, 330:109-113.
Gribkoff et al., "The Need for New Approaches in CNS Drug Discovery: Why Drugs Have Failed, and What Can Be Done to Improve Outcomes," Neuropharmacology, Jul. 1, 2017, 120:11-19.
Knonfal et al., "Pilot Phase II study of mazindol in children with attention deficit/hyperactivity disorder," Drug Design, Development and Therapy, 2014, 8:2321-2332.
Miller et al., "Mazindol in treatment-refractory depression," Abstract of the Annual Meeting of the Society for Neuroscience, Society for Neuroscience, Washington DC, Jan. 1, 1991, 17(102):1436, Abstract 569.10.
Quitkin et al., "Chapter 1: Stimulants," Current Psychotherapeutic Drugs, 1998, 25 pages.
Wigal et al. "A Double-Blind, Placebo-Controlled, Phase II Study to Determine the Efficacy, Safety, Tolerability and Pharmacokinetics of a Controlled Release (CR) Formulation of Mazindol in Adults with DSM-5 Attention-Deficit/Hyperactivity Disorder (ADHD)," CNS Drugs, 2018, 32:289-301.
Zhao et al., "Comparison of [Dmt1]DALDS and DAMGO in Binding and G Protein Activation at μ, δ and κ Opioid Receptors," The Journal of Pharmacology and Experimental Therapeutics, 2003, 307(3):947-954.

* cited by examiner

*Primary Examiner* — Umamaheswari Ramachandran
(74) *Attorney, Agent, or Firm* — Foley & Lardner LLP

(57) ABSTRACT

The invention comprises a method of treatment of CNS disorders by a pharmaceutical agent exhibiting combined noradrenergic, serotonergic or dopaminergic reuptake transporter inhibitory and μ-opioid agonistic activity.

4 Claims, 3 Drawing Sheets

IC50 = 6.9E-07 M nH = 0.8

METHOD OF TREATMENT OF CNS DISORDERS

CROSS-REFERENCE TO RELATED APPLICATIONS

This application is a Continuation of U.S. application Ser. No. 16/678,848, filed Nov. 8, 2019, which is a Continuation of U.S. application Ser. No. 14/795,983, filed Jul. 10, 2015, now abandoned, which is a Continuation of U.S. application Ser. No. 13/512,706, filed Aug. 8, 2012, now abandoned, which is the U.S. National Stage of PCT/US2010/058745, filed Dec. 2, 2010, which claims priority to U.S. Provisional Application No. 61/282,011, filed Dec. 2, 2009.

JOINT RESEARCH AGREEMENT

Inventions described in this application were made by or on behalf of Supernus Pharmaceuticals, Inc., which was a party to a joint research agreement with Afecta Pharmaceuticals, Inc. that was in effect on or before the date such inventions were made and such inventions were made as a result of activities undertaken within the scope of the joint research agreement.

BACKGROUND

Mazindol (5-(p-chloropheny)-2,5-dihydro-3H-imidazo[2, 1-a] isoindol-5-ol) is a monoamine reuptake inhibitor originally marketed as Degonan by Slovakofarma (Czechoslovakia), Mazanor by Wyeth-Ayerst (USA), Mazindol by Polfa (Poland), Sanorex by Sandoz (USA), and Teronac by Wander (Germany and the UK). Mazindol was also approved under an orphan drug indication for Duschene Muscular Dystrophy in the USA.

Mazindol has specific inhibitory binding activity at the dopamine, noradrenergic and serotonergic reuptake transporters as well as moderately potent binding at the H1 receptor. The present invention is predicated on the unexpected discovery that mazindol may be effective in the treatment of several CNS disorders with nominal, if any, side effects.

SUMMARY OF THE INVENTION

In one aspect, the present invention provides a method of treatment of major depressive disorder, generalized anxiety disorder, panic disorder, social anxiety disorder, obsessive compulsive disorder, autism, aggression, intermittent explosive disorder, attachment disorder, attention deficit hyperactivity disorder and schizophrenia by an agent exhibiting noradrenergic (NRI), serotonergic (SRI) or dopaminergic reuptake transporter inhibitory (antagonist) activity (DRI) in conjunction with μ-opioid receptor agonist activity.

In another aspect, the current invention provides a novel method for treatment of the aforementioned CNS disorders by administering a formulation of mazindol.

DETAILED DESCRIPTION OF THE INVENTION

Figure 1:
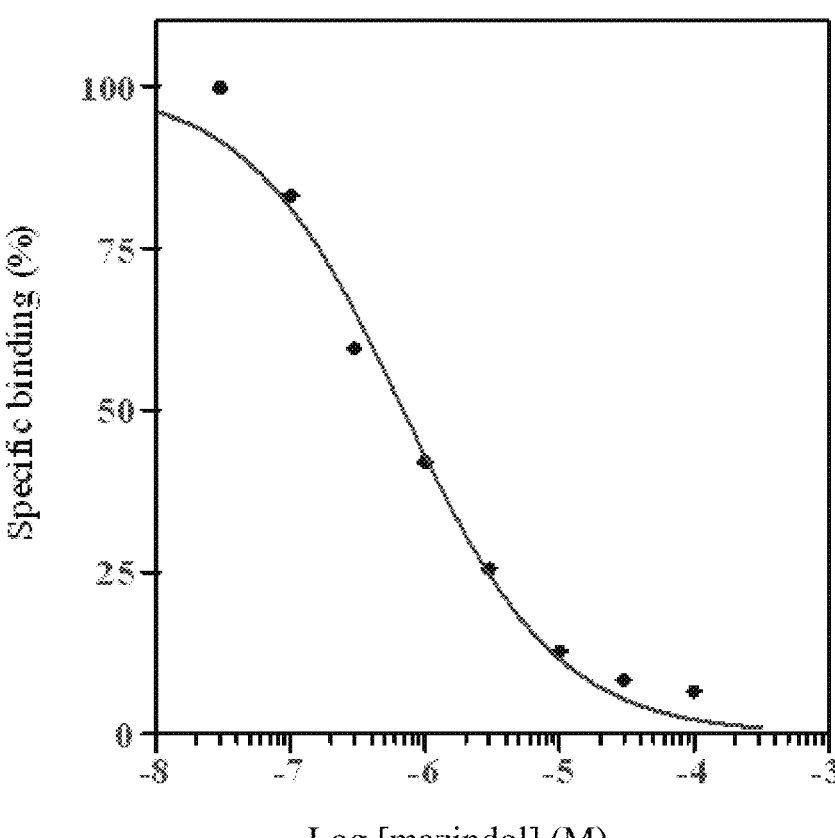
FIG. 1 shows a competition curve obtained for mazindol with the human μ-opioid receptor.

Unless otherwise specified, "a" or "an" means "one or more."

In one embodiment, the invention comprises a method of treatment of major depressive disorder, generalized anxiety disorder, panic disorder, social anxiety disorder, obsessive compulsive disorder, autism, aggression, intermittent explosive disorder, attachment disorder, attention deficit hyperactivity disorder and schizophrenia by an agent exhibiting noradrenergic (NRI), serotonergic (SRI) or dopaminergic reuptake transporter inhibitory (antagonist) activity (DRI) and μ-opioid receptor agonist activity.

The pharmaceutical agents useful for the practice of the current invention are identified by a process comprising the steps of: (1) selecting one or a combination of active agents with known activity inhibiting with the noradrenergic, serotonergic or dopaminergic reuptake transporters; (2) conducting a receptor screening assay on the selected agent(s) to identify whether the agent is active in binding the μ-opioid receptor; (3) determining if the said activity is agonistic or antagonistic; (4) selecting among the screened active agents at least one that targets the most diverse types of CNS-disease associated receptors; (5) and optimizing the total dosage of the selected active agent(s).

In another embodiment, the pharmaceutical agent is mazindol, as it was unexpectedly discovered that in addition to the well documented NRI, SRI and DRI activity, mazindol exhibits specific agonist activity at the μ-opioid receptor. The novel receptor activity of mazindol was evaluated as described in the Example (below).

In yet a further embodiment, the invention provides a formulation of mazindol for the treatment of CNS disorders. The formulations of the current invention may be suitable for oral, intravenous, intramuscular or transdermal administration and may be administered from 1 to 3 times a day. The total daily dose of mazindol constitutes from 0.1 mg/day to 20 mg/day, preferably from 0.5 mg/day to 6 mg/day.

EXAMPLE

Evaluation of a Novel Receptor Activity of Mazindol

The novel receptor activity of mazindol was evaluated as follows:

A heterologous competition assay was used to determine the relative affinity of mazindol for opioid receptors. Briefly, recombinant μ-, κ- or δ-opioid receptors were expressed in a CHO cell line. The receptors were then saturated with a tritiated receptor-specific ligand at concentrations known to be saturating. Thereupon, 10 μM mazindol was added to the cells in the presence of non-specific ligand and incubated. In this way, mazindol was allowed to "compete" with the receptor-specific ligand, such that greater displacement (i.e., % inhibition) is indicative of greater binding strength of mazindol at a given receptor. "Specific binding" refers here to the difference in the binding of the ligand to the receptors in the presence or absence of an excess of the mazindol. The conditions and results of the assays are summarized in the Table 1.

TABLE 1

| Conditions of the displacement assay at select opioid receptors for mazindol | | | | | |
| --- | --- | --- | --- | --- | --- |
| Receptor | Ligand | Conc. | Non-specific | Incubation | % Inhib. | Detection method |
| Delta2(h) | [3H] [D-Ala$^2$, D-Leu$^5$] enkephalin | 0.5 nM | Naltrexone (10 μM) | 120 min/22° C. | 14 | Scintillation Counting |
| Kappa (rat) | [3H]U 69593 | 1 nM | Naloxone (10 μM) | 60 min/22° C. | 33 | Scintillation Counting |
| μ(h) | [3H] Ala$^2$-MePhe$^4$-Gly$^5$-Enkephalin | 0.5 nM | Naloxone (10 μM) | 120 min/22° C. | 84 | Scintillation Counting |

The affinity of mazindol for the μ-opioid receptor was further characterized by determining the IC50 (i.e., the concentration of mazindol that can inhibit 50% of control specific binding). For this experiment, a range of mazindol concentrations was selected for the ligand blocking assay. The IC50 was determined using non-linear regression analysis of the competition curves using a Hill equation curve fitting $(Y=D+[(A-D)/(1+(C/C50)nH)]$, where Y=specific binding, D=minimum specific binding, A=maximum specific binding, C=compound concentration, C50=IC50, and nH=slope factor). The inhibition constants Ki were calculated using Cheng Prusoff equation. Ki is defined as the concentration of the competing ligand (mazindol) that bound to half the binding sites at equilibrium in the absence of radioligand or other competitors. The results of the affinity assay are summarized in Tables 2 and 3 and in FIG. 1.

TABLE 2

| Concentration response for the binding of mazindol at the μ-opioid receptor. | | | |
| --- | --- | --- | --- |
| Mazindol (M) | 1$^{st}$ test | 2$^{nd}$ Test | Mean |
| 3.0E−08 | 102.1 | 97.5 | 99.8 |
| 1.0E−07 | 83.2 | 83.2 | 83.2 |
| 3.0E−07 | 58.2 | 60.9 | 59.5 |
| 1.0E−06 | 42.4 | 41.7 | 42.0 |
| 3.0E−06 | 24.7 | 26.4 | 25.5 |
| 1.0E−05 | 12.6 | 13.0 | 12.8 |
| 3.0E−05 | 9.1 | 7.6 | 8.3 |
| 1.0E−04 | 5.8 | 7.4 | 6.6 |

TABLE 3

| Summary of IC50 determination at the μ-opioid receptor. | | | | |
| --- | --- | --- | --- | --- |
| | | IC50(M | Ki (M) | nH |
| M (h) (MOP) (agonist site) | mazindol | 6.9E−07 | 2.8E−07 | 0.8 |

The nature of the binding (agonist or antagonist) was next determined. Briefly, tissue preparations were suspended in 20 ml organ baths filled with an oxygenated (95% O2 and 5% CO2) and pre-warmed (37° C.) physiological salt solution of the following composition (in mM): NaCl 118.0, KCl 4.7, MgSO4 1.2, CaCl2 2.5, KH2PO4 1.2, NaHCO3 25.0 and glucose 11.0 (pH 7.4). In the μ-receptor assay, yohimbine (1 μM), propranolol (1 μM), nor-binaltorphimine (0.01 μM), methysergide (1 μM), ondansetron (10 μM) and GR113808 (0.1 μM) and indomethacin (1 μM) were also present throughout the experiments and to block the alpha2-adrenergic, beta-adrenergic, kappa-opioid, 5-HT1/5-HT2, 5-HT3 and 5-HT4 receptors, and to prevent prostanoid release respectively.

The tissues were connected to force transducers for isometric tension recordings. They were stretched to an optimal resting tension, then allowed to equilibrate for 30 min during which time they were washed repeatedly and the tension readjusted. Thereafter, appropriate electrical stimulation was delivered to the tissues using a constant current stimulator.

The experiments were carried out using semi-automated isolated organ systems possessing eight organ baths, with multichannel data acquisition.

Test for Agonist Activity

Tissues were exposed to a submaximal concentration of the respective reference agonist to verify responsiveness and to obtain a control response. Following extensive washings and recovery of control twitch contractions, the tissues were exposed to increasing concentrations of mazindol or the same agonist. The different concentrations were added cumulatively and each was left in contact with the tissues until a stable response was obtained or for a maximum of 15 min. Where an agonist-like response was obtained, the respective reference antagonist was tested against the highest concentration of mazindol to confirm the involvement of the receptor studied in this response.

Test for Antagonist Activity

The tissues were exposed to a submaximal concentration of the respective reference agonist to obtain a control response.

After stabilization of the agonist-induced response, the tissues were exposed to several increasing concentrations of mazindol or the respective reference antagonist. The different concentrations were added cumulatively and each was left in contact with the tissues until a stable effect was obtained or for a maximum of 15 min.

Where it occurred, an inhibition of the agonist-induced response caused by mazindol indicated an antagonist activity at the receptor studied.

Analysis and Expression of Results

The parameter measured was the maximum change in the amplitude of the electrically-evoked twitch contractions induced by each compound concentration.

The results are expressed as a percent of the control response to the reference agonist (mean values).

The EC50 values (concentration producing a half-maximum response) and IC50 values (concentration causing a half-maximum inhibition of the response to the reference agonist) were determined by linear regression analysis of the concentration-response curves.

Figure 2:
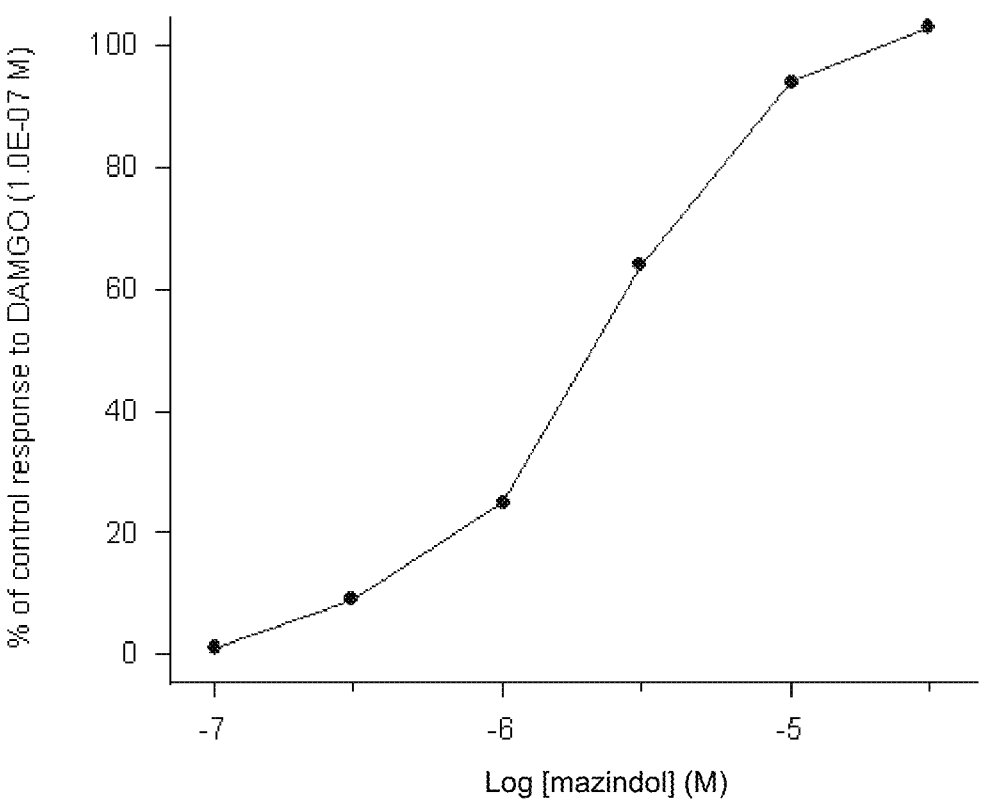
FIG. 2 shows the agonist effect of mazindol via a concentration-response curve for the effect of mazindol on the twitch contraction amplitude in the guinea pig ileum.
Figure 3:
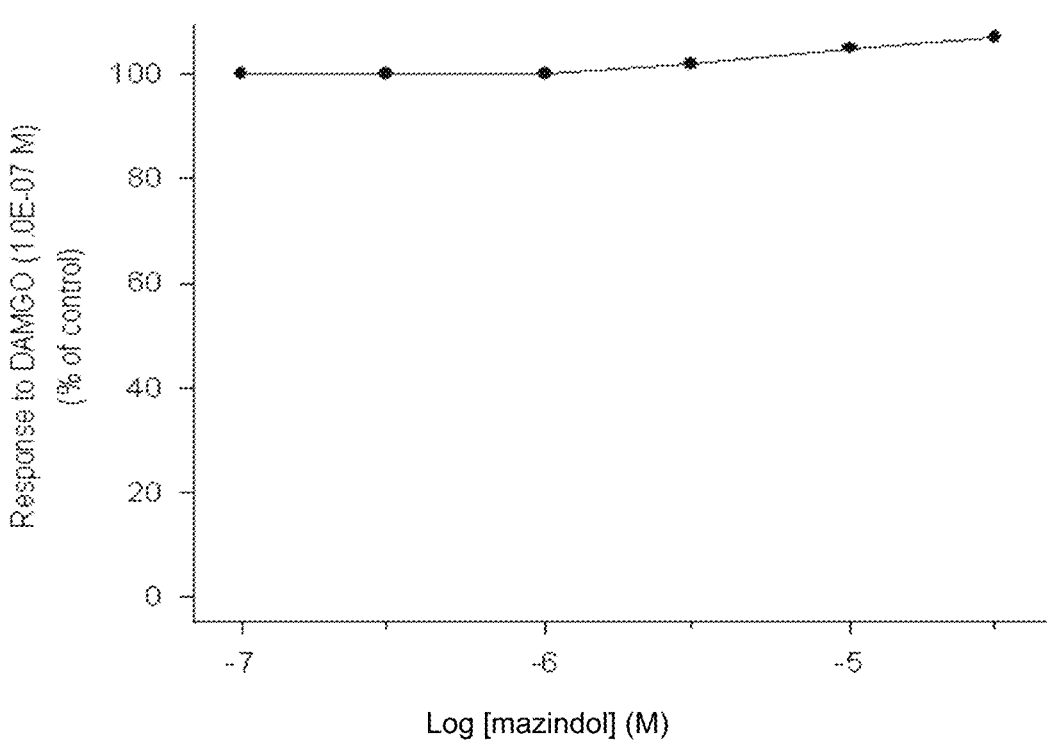
FIG. 3 shows the antagonist effect of mazindol via a concentration-response curve for the effect of mazindol on the DAMGO—induced decrease in twitch contraction amplitude in the guinea pig ileum.

Mazindol caused a concentration-dependent decrease in the twitch contraction amplitude, which was fully reversed by naloxone. It did not reverse the DAMGO-induced decrease in twitch contraction amplitude but caused a further decrease at concentrations higher than 1.0E-06 M. These results indicate that mazindol behaves as an agonist at the μ-opioid receptors in this tissue. Results of these assays are demonstrated in Tables 4 and 5 and in FIGS. 2 and 3.

TABLE 4

Effects of mazindol investigated for agonist and antagonist activities at the μ-opioid receptors in the guinea pig ileum
Evaluation of agonist activity

| Compounds | Control response to DAMGO (1.0E–07M) | Responses to Evaluation of agonist activity increasing concentrations of the compounds (M) | | | | | | +Naloxone (1.0E–07M) |
|---|---|---|---|---|---|---|---|---|
| mazindol | 100 | 1.0E–07 1 | 3.0E–07 9 | 1.0E–06 25 | 3.0E–06 64 | 1.0E–05 94 | 3.0E–05 103 | 3.0E–05M 5 |
| DAMGO | 100 | 1.0E–09 14 | | 1.0E–08 62 | | 1.0E–07 104 | | 1.0E–07M –10 |

| | to DAMGO (1.0E–07M) | Evaluation of agonist activity increasing concentrations of the compounds (M) | | | | | |
|---|---|---|---|---|---|---|---|
| mazindol | 100 | 1.0E–07 100 | 3.0E–07 100 | 1.0E–06 100 | 3.0E–06 102 | 1.0E–05 105 | 3.0E–05 107 |
| Naloxone | 100 | 5.0E–09 88 | | 2.0E–08 40 | | 1.0E–07 –5 | |

The results are expressed as a percent of the control response to DAMGO (decrease in twitch contraction amplitude) (mean values; n=2).

TABLE 5

$EC_{50}$ and $IC_{50}$ values determined for mazindol in the μ-opioid receptor bioassay

| Compound | Agonist activity $EC_{50}$ value | Antagonist activity $IC_{50}$ value |
|---|---|---|
| Mazindol | 2.0E–06 M | no antagonist effect |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating ADHD in a mammalian subject comprising administering an effective dose of mazindol to the mammalian subject, wherein the effective dose is an oral daily dose of 0.1 to 0.5 mg of mazindol.

2. The method of claim 1, wherein the oral daily dose is administered as 1 to 3 doses.

3. The method of claim 1, wherein the oral daily dose is administered as 1 dose.

4. The method of claim 1, wherein the oral daily dose is administered as 2 doses.

* * * * *